(12) United States Patent
Kakuda et al.

(10) Patent No.: US 6,333,438 B1
(45) Date of Patent: Dec. 25, 2001

(54) PROCESS FOR PRODUCING ADAMANTANOLS

(75) Inventors: Minoru Kakuda, Chiba-ken; Takanobu Okamoto, Ibaraki-ken; Takashi Onozawa, Ibaraki-ken; Hiroshi Kurata, Ibaraki-ken, all of (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 09/617,293

(22) Filed: Jul. 14, 2000

(30) Foreign Application Priority Data

Jul. 16, 1999 (JP) .................................................. 11-202796

(51) Int. Cl.$^7$ .................................................. C07C 35/22
(52) U.S. Cl. ............................................................ 568/818
(58) Field of Search .............................................. 568/818

(56) References Cited

U.S. PATENT DOCUMENTS

| | | |
|---|---|---|
| 6,111,097 | 8/2000 | Nagashima et al. . |
| 6,187,967 * | 2/2001 | Kakuda .................................. 568/818 |

FOREIGN PATENT DOCUMENTS

| | | |
|---|---|---|
| 2-104553 | 4/1990 | (JP) . |
| 3-118342 | 5/1991 | (JP) . |
| 5-51334 | 3/1993 | (JP) . |
| 8-38909 | 2/1996 | (JP) . |
| 9-87216 | 3/1997 | (JP) . |
| 2678784 | 8/1997 | (JP) . |
| 9-327626 | 12/1997 | (JP) . |
| 10-286467 | 10/1998 | (JP) . |

OTHER PUBLICATIONS

Mello, et al., "Oxidations by Methyl(trifluromethyl)dioxirane. 2.$^1$ Oxyfunctionalization of Saturated Hydrocarbons", J. Am. Chem. Soc., vol. 111, No. 17, 1989, pp. 6749–6757.
U.S. application Serial No. 09/493207, filed Jan. 28, 2000.

\* cited by examiner

*Primary Examiner*—Michael L. Shippen
(74) *Attorney, Agent, or Firm*—Antonelli, Terry, Stout & Kraus, LLP

(57) ABSTRACT

A process for efficiently separating and recovering a ruthenium compound used as the catalyst in the production of adamantanols. The adamantanols are produced by hydroxylating an adamantane compound in the presence of a ruthenium compound and a salt of hypochlorous acid in a water/organic solvent two-phase system. The hydroxylation product liquid is added with an oxidizing agent to allow the ruthenium compound to be extracted into the organic phase. The ruthenium compound is separated and recovered from the organic phase. Alternatively, the ruthenium compound is back-extracted into the aqueous phase by adding an aqueous alkali solution to the organic phase. Then, the ruthenium compound is separated and recovered from the aqueous phase.

14 Claims, No Drawings

PROCESS FOR PRODUCING ADAMANTANOLS

FIELD OF THE INVENTION

The present invention relates to a process for producing adamantanols useful as raw materials for high performance polymers, synthetic lubricants and plasticizers, and as intermediates for preparing organic chemicals of pharmaceutical and agricultural use.

BACKGROUND OF THE INVENTION

As the method of producing adamantanepolyols, proposed are a method using chromic acid (Japanese Patent Application Laid-Open No. 2-104553), hydrolysis of a brominated adamantane (Japanese Patent Application Laid-Open No. 3-118342 and Japanese Patent No. 26787849), air-oxidation of adamantane compounds in the presence of imide compound catalyst (Japanese Patent Application Laid-Open Nos. 8-38909, 9-327626 and 10-286467), metalloporphyrin-catalyzed oxidization of adamantane compounds by air (Japanese Patent Application Laid-Open No. 9-87216), a method of using ruthenium catalysts and peroxy acids (Japanese Patent Application Laid-Open No. 5-51334), a method of using dioxirane derivatives (J. Am. Chem. Soc., 111, 6749 (1989)), etc. However, the major problems of the proposed methods are in the complicated reaction systems and low yields.

In U.S. patent application Ser. No. 09/493,207 (European Patent Application No. 00100253.4), the inventors have proposed a process for producing adamantanols in high yields by hydroxylation of adamantane compounds in a water/organic two-phase system in the presence of a ruthenium compound and a salt of hypochlorous acid. The ruthenium used in the process is a very expensive transition metal. Therefore, loss of the ruthenium compound must be minimized in the production of adamantanols and it is quite important for the industrial application of the process to ensure the recovery and reuse of the ruthenium compound.

SUMMARY OF THE INVENTION

An object of the present invention is to provide a process for efficiently separating and recovering a ruthenium compound used as the catalyst in the process for producing adamantanols by hydroxylation of adamantane compounds in a water/organic two-phase system in the presence of a ruthenium compound and a salt of hypochlorous acid.

As a result of extensive study on the process for producing adamantanols by hydroxylation of adamantane compounds in a water/organic two-phase system in the presence of a ruthenium compound and a salt of hypochlorous acid, the inventors have found that the ruthenium compound is extracted into the organic phase by adding an oxidizing agent to the hydroxylation product liquid. It has been further found that the ruthenium compound is back-extracted into an aqueous phase by adding an aqueous alkali solution to the organic phase containing the extracted ruthenium compound. The present invention has been completed based on these findings.

Thus, in a first aspect of the present invention, there is provided a process for producing adamantanols, comprising the steps of (1) hydroxylating an adamantane compound in a water/organic two-phase system in the presence of a ruthenium compound and a salt of hypochlorous acid, thereby obtaining a hydroxylation product liquid; (2) mixing the hydroxylation product liquid with an oxidizing agent, thereby obtaining an extraction mixture; and (3) permitting the extraction mixture to separate into an organic phase and an aqueous phase, thereby extracting the ruthenium compound into the organic phase.

In a second aspect of the present invention, there is provided a process for producing adamantanols, in which the process mentioned above is followed by a step of mixing the organic phase containing the extracted ruthenium compound with an aqueous alkali solution, thereby back-extracting the ruthenium compound into an aqueous phase; and a step of recovering the ruthenium compound from the aqueous phase.

DETAILED DESCRIPTION OF THE INVENTION

In the present invention, the starting adamantane compounds are represented by the following formula:

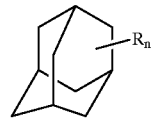

wherein R is independently alkyl group, aryl group, cycloalkyl group, alkoxy group, aryloxy group, acyloxy group or halogen atom, and suffix "n" is an integer from 0 to 14, with the proviso that at least two bridge-head carbons are not substituted by R.

In the above formula, the alkyl group may be $C_1$–$C_{10}$ alkyl such as methyl, ethyl, propyl, butyl and hexyl. The aryl group may be phenyl and naphthyl, and the cycloalkyl may be cyclohexyl or cyclooctyl. The alkoxy group may be $C_1$–$C_{10}$ alkoxy such as methoxy, ethoxy, propoxy, butoxy and hexyloxy. The aryloxy group may be phenoxy. The acyloxy group may be $C_2$–$C_6$ acyloxy such as acetyloxy, propionyloxy and butyryloxy. The halogen atom may be chlorine, bromine and iodine.

The adamantanols referred to in the present invention may include adamantanemonol, adamantanediol, adamantanetriol and adamantanetetraol, and more specifically, 1-adamantanol, 1,3-adamantanediol, 1,2-adamantanediol, 1,4-adamantanediol, etc. The adamantanols may have a substituent as mentioned in the definition of R.

In the present invention, the adamantane compounds are hydroxylated by a ruthenium compound of high oxidation state of VI to VIII which is generated by the reaction of a ruthenium compound and a salt of hypochlorous acid. The ruthenium compound usable in the present invention may include metallic ruthenium, ruthenium oxides such as ruthenium dioxide (IV) and ruthenium tetraoxide (VIII); ruthenates such as sodium ruthenate (VI); ruthenium (III) hydroxide; ruthenium halides such as ruthenium (III) chloride, ruthenium (III) bromide and ruthenium (III) iodide; ruthenium (IV) sulfate; ruthenium (III) nitrate; ruthenium carboxylates such as ruthenium (III) acetate; and ruthenium complexes such as ammonium hexachlororuthenate (III), potassium hexachlororuthenate (III), ammonium pentachloroaquaruthenate (III), potassium pentachloroaquaruthenate (III), potassium pentachloronitrosylruthenate (III), hexaammineruthenium (III) chloride, hexaammineruthenium (III) bromide, hexaammineruthenium (III) iodide, nitrosylpentaammineruthenium (III) chloride, hydroxonitrosyltetraammineruthenium (III) nitrate, ruthenium (IV) ethylenediaminetetraacetate and ruthenium (0) dodecacarbonyl. The above ruthenium compounds may be anhydrous or hydrated.

The ruthenium compound may be used alone or in combination of two or more. The ruthenium compound is used in an amount of 0.01 to 2.00 mol, preferably 0.05 to 0.40 mol per one mol of the starting adamantane compound.

Sodium hypochlorite is preferably used in the present invention as the salt of hypochlorous acid. Sodium hypochlorite is usually used as aqueous solution in a concentration of 0.01 to 2.00 mmol/g, preferably 0.07 to 1.00 mmol/g, and added 0.5 to 4.0 mol, preferably 1.0 to 3.0 per one mol of the starting adamantane compound.

The organic solvent usable in the present invention may be selected from good solvents for the ruthenium compound of high oxidation state, which are less compatible with water and inert to hydroxylation of the adamantane compounds. If highly compatible with water, the recovery of the solvent becomes costly, and the reaction hardly proceeds if the organic solvent is poor in dissolving the ruthenium compound of high oxidation state. Examples of the organic solvent are alkyl halides such as dichloromethane, 1,2-dichloroethane, chloroform, carbon tetrachloride, 1,1,2-trichloroethane, 1,4-dichlorobutane, and 1,6-dichlorohexane; esters such as methyl acetate, ethyl acetate and isopropyl acetate; aryl halides such as hexachlorobenzene and 1,1,1-trifluorotoluene; and hydrocarbons such as hexane, heptane and octane. The above organic solvent may be used alone or in combination of two or more. The amount of the solvent to be used is 0.1 to 20 parts by weight, preferably 1 to 10 parts by weight per one part by weight of the starting adamantane compound.

The hydroxylation of the adamantane compound is carried out at 10 to 80° C., preferably 40 to 70° C. in a water/organic two-phase system. The weight ratio of water and the organic solvent in the two-phase system is preferably 1:2 to 1:20.

In the present invention, an oxidizing agent is added to the hydroxylation product liquid to convert the ruthenium compound into high oxidation state having a high affinity to the organic solvent. With such a treatment, the ruthenium compound is easily transferred into the organic phase. If required, an aqueous alkali solution may be added to the organic phase to back-extract the ruthenium compound into an aqueous phase for recovery.

The oxidizing agent is at least one compound selected from the group consisting of molecular halogens, halogen oxides, perhalogenic acids and salts thereof, halogenic acids and salts thereof, halogenous acids and salts thereof, hypohalogenous acids and salts thereof, molecular oxygen, hydrogen peroxide, peracids, hydroperoxides, peroxides, persulfuric acid and salts thereof, and ferricyanides. Examples of the oxidizing agent include molecular halogens such as chlorine and bromine; halogen oxides such as dichlorine monooxide, chlorine dioxide and dibromine monooxide; perhalogenic acids such as periodic acid and perchloric acid; halogenic acids such as bromic acid and chloric acid; halogenous acids such as bromous acid and chlorous acid; hypohalogenous acids and salts thereof such as hypobromous acid, hypochlorous acid and sodium hypochlorite; molecular oxygen; hydrogen peroxide; peracids such as performic acid, peracetic acid and perbenzoic acid; hydroperoxides such as cumene hydroperoxide and benzyl hydroperoxide; peroxides such as t-butyl benzyl peroxide and dibenzoyl peroxide; persulfuric acids such as peroxydisulfuric acid and Caro's acid; and ferricyanides such as potassium ferricyanide and sodium ferricyanide. Among these compounds, sodium hypochlorite which is also used in hydroxylation of the adamantane compound is preferable due to its easy availability, low cost and easiness of treatments after the reaction.

The addition amount of the oxidizing agent is 0.01 to 50 mol, preferably 0.05 to 30 mol per one mol of the ruthenium compound. When less than the above range, the ruthenium compound fails to maintain its high oxidation state during the phase separation of the hydroxylation product liquid, and as a result thereof, the ruthenium compound transfers into the aqueous phase. When exceeding the above range, the selectivity to adamantanols decreases due to side reactions. The oxidizing agent is preferably added to the hydroxylation product liquid as an aqueous solution in 0.01 to 10.0 mmol/g concentration.

The extraction is carried out at 10 to 80° C. under ordinary pressure by mixing, stirring or shaking. After completing the extraction, the extraction mixture is permitted to separate into an organic phase and an aqueous phase.

The organic phase containing the ruthenium compound of high oxidation state can be used in the next hydroxylation of the adamantane compound without any further treatments. Alternatively, the ruthenium compound may be separated and recovered from the organic phase and then reused in the next run. The ruthenium compound of high oxidation state can be efficiently separated from the organic phase by adding an aqueous alkali solution. More specifically, by adding an aqueous alkali solution to the organic phase and adjusting the pH of the aqueous phase to 9 or higher, preferably 10 or higher, the ruthenium compound of high oxidation state is back-extracted into the aqueous phase. In the back-extraction procedure, an oxidizing agent may be added to maintain the high oxidation state of the ruthenium compound.

The concentration of the aqueous alkali solution is preferably 0.1 to 50.0% by weight, more preferably 1.0 to 30.0% by weight. Generally, 0.001 to 5.0 g of the aqueous alkali solution is added per one gram of the organic phase.

Examples of the alkalis include metal hydroxides such as sodium hydroxide, potassium hydroxide, lithium hydroxide and barium hydroxide; ammonia; alkylamines such as triethylamine; and tetraalkylammonium hydroxides such as tetramethylammonium hydroxide, tetraethylammonium hydroxide, tetrapropylammonium hydroxide and tetrabutylammonium hydroxide. Of the above alkalis, sodium hydroxide and potassium hydroxide are preferable.

Although the higher the extraction temperature, the higher the extraction speed. Since the ruthenium compound of high oxidation state is volatile, the extraction temperature is 0 to 100° C., preferably 10 to 80° C. under ordinary pressure. The mixing and separation of the organic phase and the aqueous alkali solution are conducted in known extraction apparatus such as a reactor equipped with a stirring device, a single- or multi-stage mixer-settler and an extraction column.

After adjusting the pH to 7 or lower by addition of an acid, the aqueous phase containing the ruthenium compound of high oxidation state may be reused in the next hydroxylation of the adamantane compound without any further treatments. Alternatively, the ruthenium compound may be separated and recovered from the aqueous phase and then reused in the next reaction.

The ruthenium compound of high oxidation state back-extracted into the aqueous phase can be precipitated as a ruthenium compound of low oxidation state by the addition of a reducing agent. The precipitated ruthenium compound is separated and recovered from the aqueous phase. The reducing agent may be a usual reducing agent such as salts of sulfurous acid, hydrazine and salts thereof, hydroxylamine and salts thereof, hydrogen peroxide, quinones and lower alcohols such as methanol, ethanol and 2-propanol.

Generally, 0.001 to 0.1 g of the reducing agent is added per one gram of the aqueous phase containing the back-extracted ruthenium compound.

The precipitated ruthenium compound in the aqueous phase is recovered as solid matter or slurry using a filter, a sedimentation separator or a centrifugal separator such as a liquid cyclone. The recovered solid matter or slurry may be dried by an evaporator, etc. The ruthenium compound recovered as slurry, solid matter or dried product is reused in the next production of the adamantanols without further treatments or as a dispersion in water, etc.

The present invention will be described more specifically with reference to the following examples. However, it should be noted that the present invention is not intended to limit thereto.

EXAMPLE 1

Into a 2-liter jacketed glass reactor equipped with a stirrer, a thermometer, a Dimroth condenser and a pH electrode, were placed 102 g (0.75 mol) of adamantane, 550 ml of dichloroethane, 6.3 g of ruthenium chloride n-hydrate (2.2 g ruthenium) and 58 g of water. To the resultant mixture, 2,095 g of aqueous solution of sodium hypochlorite (0.72 mmol/g) were added dropwise at 50° C. over 190 minutes. After the addition was completed, the reaction mixture was added with 15 g of aqueous solution of sodium hypochlorite (0.72 mmol/g) and permitted to separate into the dichloroethane phase and the aqueous phase. The dichloroethane phase contained 2.1 g of ruthenium and the aqueous phase contained 0.1 g of ruthenium.

EXAMPLE 2

Into a 10-liter jacketed glass reactor equipped with a stirrer, a thermometer, a Dimroth condenser and a pH electrode, were placed 413 g (3.0 mol) of adamantane, 2,200 ml of dichloroethane, 25.7 g of ruthenium chloride n-hydrate (7.4 g ruthenium) and 360 g of water. To the resultant mixture, 8,922 g of aqueous solution of sodium hypochlorite (0.72 mmol/g) were added dropwise at 50° C. over 160 minutes. After the addition was completed, the reaction mixture was added with 16 g of aqueous solution of sodium hypochlorite (0.72 mmol/g) and permitted to separate into the dichloroethane phase and the aqueous phase. The dichloroethane phase contained 6.9 g of ruthenium and the aqueous phase contained 0.5 g of ruthenium. The dichloroethane phase was added with 2,006 g of 1% by weight aqueous solution of sodium hydroxide and 43 g of aqueous solution of sodium hypochlorite (0.72 mmol/g). After the mixture was stirred at 40° C. for 10 minutes, the mixture was permitted to separate into the dichloroethane phase and the aqueous phase. The dichloroethane phase was colorless. To the aqueous phase (pH=13), 35 g of concentrated hydrochloric acid was added to reduce the pH to 6 and then 27 g of 2-propanol was added. After allowed to stand overnight, precipitated black solid matter were collected by filtration to obtain 27.7 g of the ruthenium compound (6.9 g ruthenium).

As described above, the ruthenium compound used as the catalyst for producing the adamantanols are recovered efficiently in the process of the present invention.

What is claimed is:

1. A process for producing adamantanols, comprising the steps of:

hydroxylating an adamantane compound in a water/organic two-phase system in the presence of a ruthenium compound and a salt of hypochlorous acid, thereby obtaining a hydroxylation product liquid;

mixing the hydroxylation product liquid with an oxidizing agent, thereby obtaining an extraction mixture; and permitting the extraction mixture to separate into an organic phase and an aqueous phase, thereby extracting the ruthenium compound into the organic phase.

2. The process according to claim 1, further comprising the subsequent steps of:

mixing the organic phase containing the extracted ruthenium compound with an aqueous alkali solution, thereby back-extracting the ruthenium compound into an aqueous phase; and recovering the ruthenium compound from the aqueous phase.

3. The process according to claim 2, wherein the aqueous phase containing the back-extracted ruthenium compound is added with a reducing agent.

4. The process according to claim 3, wherein the reducing agent is at least one compound selected from the group consisting of salts of sulfurous acid, hydrazine and salts thereof, hydroxylamine and salts thereof, hydrogen peroxide, quinones and lower alcohols.

5. The process according to claim 4, wherein the lower alcohol is methanol, ethanol or propanol.

6. The process according to claim 3, wherein the reducing agent is added to the aqueous phase in an amount of 0.001 to 0.1 g per one gram of the aqueous phase.

7. The process according to claim 1, wherein the oxidizing agent is at least one compound selected from the group consisting of molecular halogens, halogen oxides, perhalogenic acids and salts thereof, halogenic acids and salts thereof, halogenous acids and salts thereof, hypohalogenous acids and salts thereof, molecular oxygen, hydrogen peroxide, peracids, hydroperoxides, peroxides, persulfuric acid and salts thereof, and ferricyanides.

8. The process according to claim 1, wherein the oxidizing agent is a salt of hypohalogenous acid.

9. The process according to claim 8, wherein the salt of hypohalogenous acid is a slat of hypochlorous acid.

10. The process according to claim 1, wherein the oxidizing agent is added to the hydroxylation product liquid in an amount of 0.01 to 50 mol per one mol of the ruthenium compound.

11. The process according to claim 2, wherein the alkali is at least one compound selected from the group consisting of sodium hydroxide, potassium hydroxide, lithium hydroxide, barium hydroxide; ammonia, triethylamine, tetramethylammonium hydroxide, tetraethylammonium hydroxide, tetrapropylammonium hydroxide and tetrabutylammonium hydroxide.

12. The process according to claim 2, wherein the alkali is sodium hydroxide or potassium hydroxide.

13. The process according to claim 2, wherein the pH of the aqueous phase is adjusted to 9 or higher by the addition of the aqueous alkali solution.

14. The process according to claim 2, wherein 0.001 to 5.0 g of the aqueous alkali solution of 0.1 to 50.0% by weight concentration is added per one gram of the organic phase.

* * * * *